US009764176B2

(12) United States Patent
Waterman

(10) Patent No.: US 9,764,176 B2
(45) Date of Patent: Sep. 19, 2017

(54) ACTIVITY FRAME

(71) Applicant: Mark Julian Waterman, Oxford (GB)

(72) Inventor: Mark Julian Waterman, Oxford (GB)

( * ) Notice: Subject to any disclaimer, the term of this patent is extended or adjusted under 35 U.S.C. 154(b) by 0 days.

(21) Appl. No.: 14/903,105

(22) PCT Filed: Jul. 1, 2014

(86) PCT No.: PCT/GB2014/051996
§ 371 (c)(1),
(2) Date: Jan. 6, 2016

(87) PCT Pub. No.: WO2015/004423
PCT Pub. Date: Jan. 15, 2015

(65) Prior Publication Data
US 2016/0121155 A1    May 5, 2016

(30) Foreign Application Priority Data

Jul. 7, 2013  (GB) .................................. 1312167.8

(51) Int. Cl.
| | | |
|---|---|---|
| A63B 19/04 | (2006.01) | |
| A63G 1/08 | (2006.01) | |
| B01J 19/00 | (2006.01) | |
| B01L 3/00 | (2006.01) | |
| G01N 33/487 | (2006.01) | |

(Continued)

(52) U.S. Cl.
CPC .......... *A63B 19/04* (2013.01); *A63B 21/4049* (2015.10); *A63G 1/08* (2013.01);
(Continued)

(58) Field of Classification Search
CPC ........ A63B 19/00; A63B 19/04; A63G 31/00; A63G 31/16; G09B 9/00; G09B 9/02
(Continued)

(56) References Cited

U.S. PATENT DOCUMENTS 3,141,669 A *  7/1964  Chul ...................... A63B 19/04
                                                    472/17
4,799,667 A    1/1989  Suchy
(Continued)

FOREIGN PATENT DOCUMENTS

DE    197 15 652    10/1998
DE    200 06 998    8/2000
(Continued)

OTHER PUBLICATIONS

International Search Report for PCT/GB2014/051996 mailed Dec. 9, 2014, six pages.
(Continued)

*Primary Examiner* — Kien Nguyen
(74) *Attorney, Agent, or Firm* — Nixon & Vanderhye P.C.

(57) ABSTRACT

An activity frame comprising a first or outer ring mounted between a pair of opposed bearings in a opposed pair of supports, for example upstanding members of a frame, the first bearings having a having a first common axis; a second or middle ring mounted between opposed bearings on the first ring, the bearings having a second common axis orthogonal to the first common axis; a third or inner ring mounted between opposed bearings on the second ring, the bearings having a third common axis orthogonal to the second axis provided with demountable restraining means to limit the movement of two or more of the rings and demountable bars to fix one or more of the rings to the frame or other fixed object.

11 Claims, 18 Drawing Sheets

(51) Int. Cl.
*A63B 21/00* (2006.01)
*A63G 1/14* (2006.01)

(52) U.S. Cl.
CPC ............ *A63G 1/14* (2013.01); *B01J 19/0046* (2013.01); *B01L 3/5088* (2013.01); *G01N 33/48721* (2013.01); *B01J 2219/00313* (2013.01); *B01J 2219/00317* (2013.01); *B01J 2219/00351* (2013.01); *B01J 2219/00585* (2013.01); *B01J 2219/00659* (2013.01); *B01J 2219/00734* (2013.01); *B01J 2219/00736* (2013.01); *B01L 2200/0642* (2013.01); *B01L 2400/086* (2013.01)

(58) Field of Classification Search
USPC ........... 472/45–47, 59, 60, 130; 434/55, 247
See application file for complete search history.

(56) References Cited

U.S. PATENT DOCUMENTS

| | | | |
|---|---|---|---|
| 5,046,721 A | 9/1991 | Altare | |
| 5,060,932 A * | 10/1991 | Yamaguchi | A63G 31/16 434/34 |
| 5,342,244 A | 8/1994 | Nelson | |
| 5,558,582 A * | 9/1996 | Swensen | G09B 9/02 472/43 |
| 2003/0125119 A1* | 7/2003 | Jones | A63F 13/08 472/60 |
| 2005/0178221 A1 | 8/2005 | Tippett | |
| 2006/0144282 A1 | 7/2006 | Casey | |

FOREIGN PATENT DOCUMENTS

| | | |
|---|---|---|
| DE | 200 06 998 | 9/2000 |
| EP | 2 394 705 | 12/2011 |
| GB | 325190 | 2/1930 |
| JP | 57-203947 | 6/1956 |
| TW | M374885 | 3/2010 |
| WO | WO 97/24163 | 7/1997 |
| WO | WO 00/20083 | 4/2000 |
| WO | WO 2012/160022 | 11/2012 |

OTHER PUBLICATIONS

Written Opinion of the Isa for PCT/GB2014/051996 mailed Dec. 9, 2014, six pages.

* cited by examiner

US 9,764,176 B2

ACTIVITY FRAME

This application is the U.S. national phase of International Application No. PCT/GB2014/051996 filed 1 Jul. 2014 which designated the U.S. and claims priority to GB Patent Application No. 1312167.8 filed 7 Jul. 2013, the entire contents of each of which are hereby incorporated by reference.

TECHNICAL FIELD

This invention relates to an activity frame. Its primary application is as a children's play frame, but a stronger unit could be used for adult keep-fit activities or for adult or children's restorative and recuperation activities.

BACKGROUND ART

PTL 0001: U.S. Pat. No. 4,799,667 A (GYROTECH CORPORATION). 1989 Jan. 24;
PTL 0002: GB 325190 A (FRIED). 1930 Feb. 11; and
PTL 0003: WO WO 00/20083 A (GEURTS). 2000 Apr. 13,
for example, describe activity frames comprising three concentric rings: a first or outer ring mounted between a pair of opposed bearings in a opposed pair of supports, for example upstanding members of a frame, the first bearings having a having a first common axis; a second or middle ring mounted between opposed bearings on the first ring, the bearings having a second common axis orthogonal to the first common axis; a third or inner ring mounted between opposed bearings on the second ring, the bearings having a third common axis orthogonal to the second axis. Such activity frames enable a person on the inner ring to execute movement in three dimensions with respect to the pair of supports.

However the play value of such an activity frame is limited in terms of the variety of activities that can be undertaken.

This invention seeks to provide an activity frame comprising three rings that can be configured in a number of different ways so opening a variety of activities.

DISCLOSURE OF INVENTION

According to the present invention an activity frame comprising a first or outer ring mounted between a pair of opposed bearings in an opposed pair of supports, the first bearings having a having a first common axis; a second or middle ring mounted between opposed bearings on the first ring, the bearings having a second common axis orthogonal to the first common axis; a third or inner ring mounted between opposed bearings on the second ring, the bearings having a third common axis orthogonal to the second axis characterised in comprising demountable restraining means to limit the movement of two or more of the rings and demountable bars to fix one or more of the rings to the frame or other fixed object allowing a range of different ring positions relative to the supports.

The pair of supports may be mounted individually in the ground, or be part of a supporting frame work which itself is supported on the ground.

In one arrangement the demountable restraining means comprises one or more clamps.

The demountable restraining means comprises spring means, such as one or more of a spring, elasticated material, and elasticated rope.

Further the demountable restraining means may comprise actuators or motors, or an actuator or motor attached to one ring and a clamp attached between the other two rings or to one other ring and a support or other fixed object.

In a first configuration the inner ring has a sphere mounted inside, so that the inner ring is round a circumference of the sphere. The sphere has an opening which may be closed and by which individuals can enter or leave the sphere. In this configuration movement of an individual within the sphere causes the inner and middle rings to rotate with respect to one another and in respect to the outer ring, allowing the sphere to undertake tumbling-like motions.

In a second configuration the inner ring has a cylindrical tub or barrel mounted therein with the inner ring being a circumference of the cylindrical tub or barrel, the outer ring is fixed in relation to the supports and the inner ring is fixed in relation to the middle ring. The cylindrical tub or barrel has an opening which may be closed by which an individual may enter of leave the cylindrical tub or barrel. In this configuration movement of an individual within the cylindrical tub or barrel causes middle rings to rotate with outer ring, allowing the cylindrical tub or barrel to rotate.

In a third configuration the inner ring is provided with a seat. Movement of the rings is controlled and restricted by one or more powered actuators or motors acting on or more of the rings. This embodiment provides a powered ride, which in its simplest form can be a swing movement, but with more than one actuator or motor connected to more than one ring can be a more complex movement.

In a fourth configuration at least two rings are connected to one another by a spring means, limiting the movement of one ring with respect to the other and tending to restore the rings to their original position with respect to one another. In this embodiment the outer ring is preferably fixed in a horizontal plane. With a platform attached to the inner ring, the platform will wobble in two dimensions when any movement occurs thereon. If the platform is attached to the middle ring wobble will be confined to one dimension.

In the fifth configuration all of the rings are fixed with respect to each other in a generally vertical plane. The rings may be either rigidly connected to each other or allowed to move freely by a limited amount, or connected to one another by spring means, including stretchable elasticated material, limiting the movement of one ring with respect to another and tending to restore the rings to their original position with respect to one another. In this embodiment the inner ring supports a platform that can be used as a tennis or other sport training device or climbing wall with the attachment of suitable hand holds.

In a sixth configuration the middle ring is fixed with respect to the outer ring and inner ring fixed in relation to the middle ring. Thus only the outer ring is free to rotate in its bearings. The inner ring has an open ended co-axial cylinder mounted therein such that the inner ring forms a circumference of the cylinder. In this configuration, individuals may run or walk on the inner surface of the cylinder causing the outer ring to rotate about its bearings. In this configuration the frame form a treadmill for exercise and keep-fit purposes.

In a seventh configuration each of the rings are fixed in a horizontal plain and with respect of one another and the outer ring fixed to its supports. A platform is attached to one or more of the rings. In this configuration the platform is fixed.

In an eighth configuration each of the rings are fixed in a horizontal plain and with respect of one another and the outer ring fixed to its supports. A water tank is supported at its top by the inner ring. In this configuration the water tank is fixed and can be used as an outdoor pool or, with the inclusion of suitable pumps and heaters, a Jacuzzi.

In each of the configurations attachments are demountable. In this way the basic three ring configuration can be adapted readily from one configuration to another. In this way a single frame can be set up for a variety of different activities.

DESCRIPTION OF DRAWINGS

Embodiments of the invention will now be described, by way of example only, with reference to the accompanying drawings, in which.

DESCRIPTION OF ILLUSTRATIVE EMBODIMENTS

Figure 1:
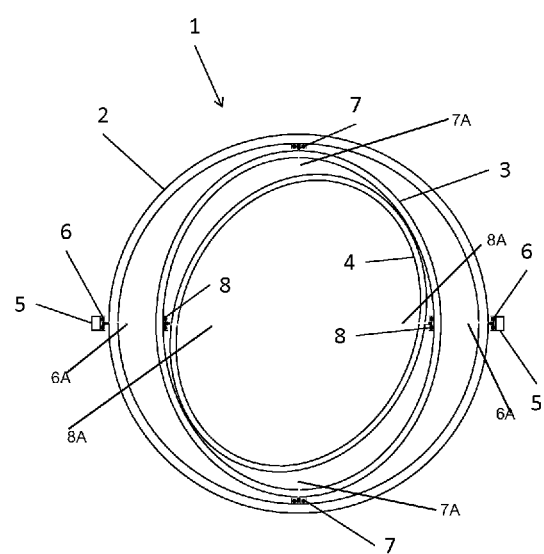
FIG. 1 shows configuration of a basic three ring the activity frame.

In FIG. 1, an activity frame 1 comprises three concentric rings, a first or outer ring 2, a second or middle ring 3, and a third or inner 4. The first or outer ring 2 is mounted between a pair of opposed bearings 6 in an opposed pair of supports 5; the first bearings 6 having a first common axis 6A. The second or middle ring 3 is mounted between opposed bearings 7 on the first ring 2; the bearings 7 having a second common axis 7A orthogonal to the first common axis 6a. The third or inner ring 4 is mounted between opposed bearings 8 on the second ring; the bearings 8 having a third common axis 8A orthogonal to the second axis 7A. The pair of opposed supports may be upstanding members of a frame or mounted separately in the ground.

Figure 2:
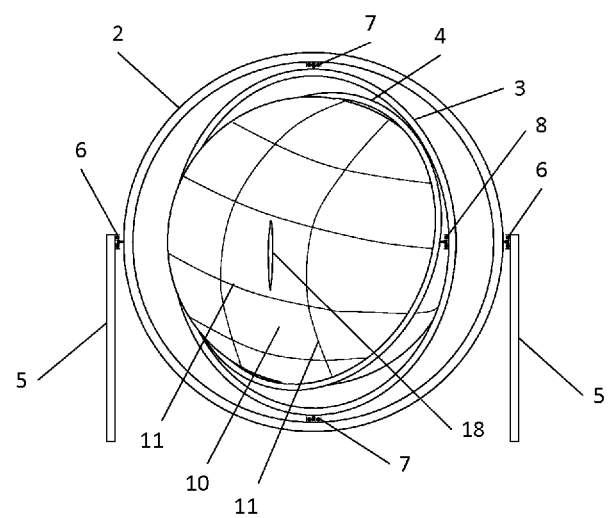
FIG. 2 shows the activity frame of FIG. 1 with a sphere is mounted inside the inner ring.

In FIG. 2 the inner ring 4 has a sphere 10 mounted inside, so that the inner ring 4 is round a circumference of the sphere 10. The sphere 10 is of a soft but strong deformable material such as padded nylon, for safety, supported in shape by a wire mesh 11. There is an opening 18 which may be closed and by which individuals can enter or leave the sphere 10. In this configuration movement of an individual within the sphere causes the inner and middle rings to rotate with respect to one another and in respect to the outer ring, allowing the sphere to undertake tumbling-like motions.

Figure 3:
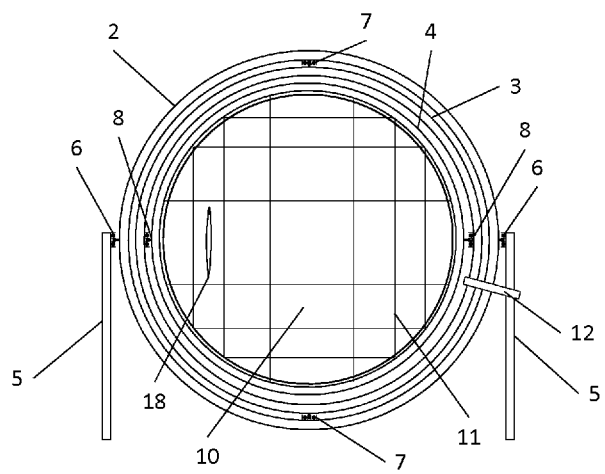
FIG. 3 is similar to FIG. 2 but with movement of the outer and middle rings locked to the mounting.

In FIG. 3, the arrangement is the same as for FIG. 2 with the addition of a mechanical clamp 12 fixing the position of the middle ring 3 to the outer ring 2 and to one of the supports 5. The sphere 10 is now free only to rotate about the axis of its pair of bearings 8.

Figure 4:
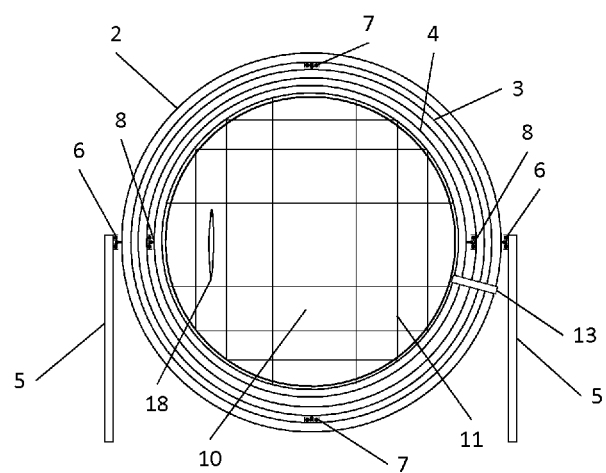
FIG. 4 is similar to FIG. 2 but with the rings locked together.

In FIG. 4, the arrangement is the same as for FIG. 1 with the addition of a mechanical clamp 13 locking together all three rings 2, 3 and 4. The sphere is free to rotate about the axis of the pair of bearings 6 supporting outer ring 2.

Figure 5:
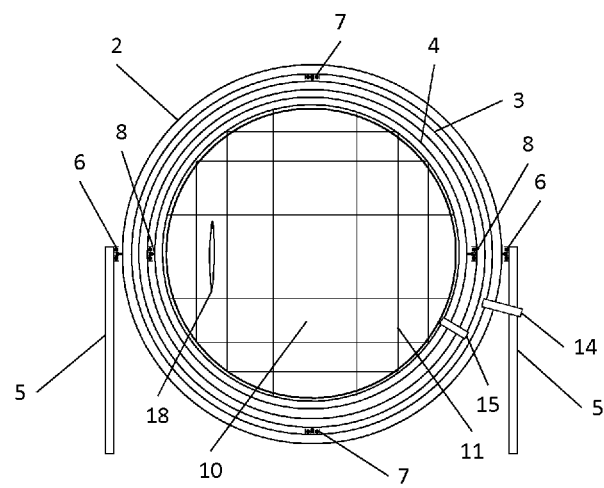
FIG. 5 is similar to FIG. 2 but with the inner ring locked to the middle ring and the outer ring also locked with respect to a support.

In FIG. 5, the arrangement is the same as for FIG. 2 with the addition of a mechanical clamp 14 locking the outer ring 2 to a support 5 in a fixed position and a mechanical clamp 15 locking the middle ring 3 to the inner ring 4. The sphere 10 is free to rotate about the axis of the pair of bearings 7 supporting the middle ring 3 on the outer ring 2.

Figure 6:
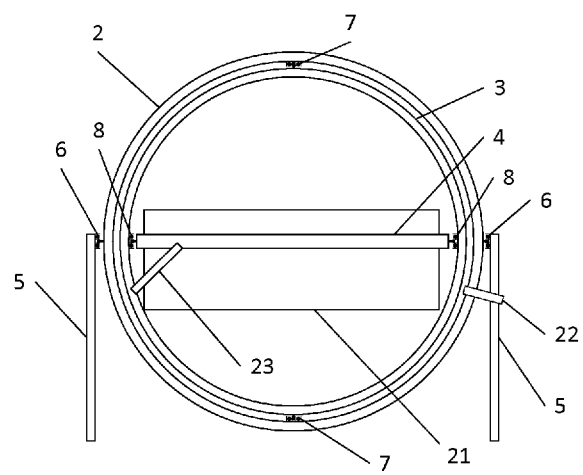
FIG. 6 is the side view of another arrangement with a cylindrical tube mounted on the inner ring.

In FIG. 6, a cylinder 21 is mounted to the inner ring 4. The outer ring 2 is connected to the supports 5 by means of a pair of two diametrically opposed bearings 6 mounted on the outer surface of the outer ring 2. The outer ring 2 is fixed with respect to a mounting 5 (or to another fixed point) by means of a mechanical clamp 22. Inner ring 4 is fixed in position relative to the middle ring 3 by means of a mechanical clamp 23. The cylinder 21 has soft inner linings or seats (not shown) and an entry point (not shown) to allow access.

Movement within cylinder 21 causes the inner ring 4 to rotate about the support bearings 7 of the middle ring 3.

Figure 7:
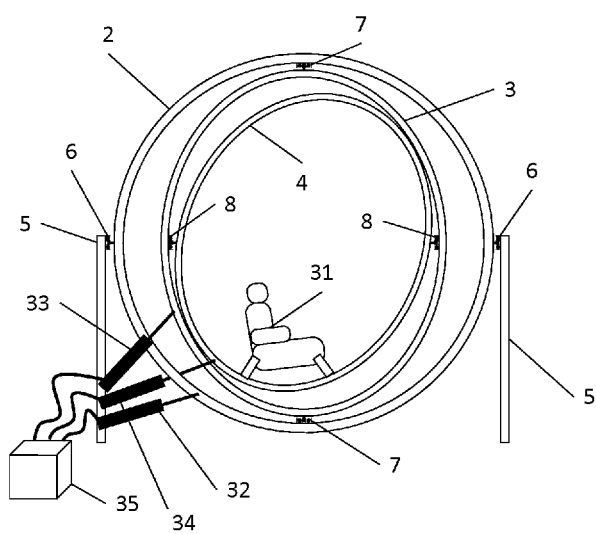
FIG. 7 is the side view of a further arrangement with a seat mounted on the inner ring and one or more actuators connected to the rings.

In FIG. 7 the overall arrangement of the rings is as described with reference to FIG. 1. In this case a seat 31 is attached to the inner ring 4. Powered actuators 32, 33, 34, supplied from a power source 35, are connected to the rings 2, 3, 4 respectively. The actuators move to and fro, causing the rings to which they are attached to move to and fro. It will be appreciated that because the rings 3 and 4 will move in more than one dimension, the actuators 32 and 33 connected to these rings will need to be mounted on flexible mountings to allow for such movement. The actuators serve both to move the rings, but also to limit the extent of their movement. As shown an individual sitting in seat 31 will be moved as a result of movement of the actuators in three dimensions. The seat would need to be supplied with seat belts or some other constraint to prevent individuals in the seat from falling out. Restricting movement of the seat to two or one dimensions is achieved by turning off one or two actuators or removing one or two actuators and clamping of rings. A video screen (not shown) can be located within line of sight of the seated individual thus simulating a range of motion based experiences such as car racing.

The actuators 32, 33 and 34 can be replaced with up to 3 stepper motors fitted at the bearing points 6, 7 and 8 and with suitable slip-rings and wiring to produce the same effect as with the powered actuators but with full powered rotation of any ring possible.

Figure 8:
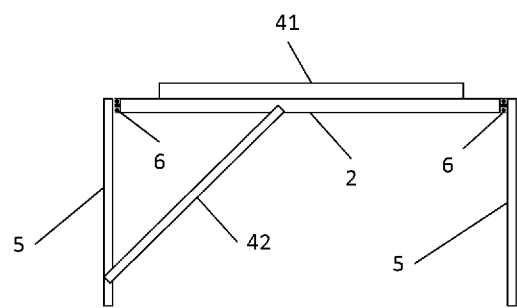
FIG. 8 shows a view of a further arrangement with a wobbling platform mounted in a horizontal position.

In FIG. 8, the three rings 2, 3, 4, and their bearing mountings 6, 7, and 8 are as described previously in FIG. 1. A platform 41 is supported by the inner ring 4, the outer ring 2 only being visible from the side view. The outer ring 2 is connected to the supports 5 by means of diametrically opposed bearings 6 mounted on the outer surface of outer ring 2. Outer ring 2 is prevented from rotating by means of a clamp 42 mounted between one support 5 and the outer ring 2.

Figure 9:
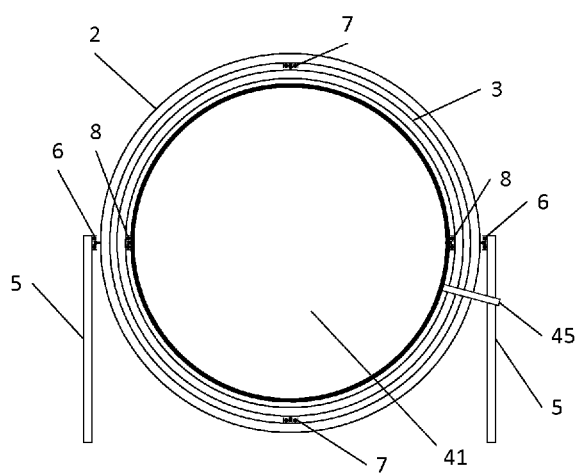
FIG. 9 shows a view of a further arrangement with a wobbling platform mounted in a vertical position.

In FIG. 9 the arrangement is the same as for FIG. 8 but with all three rings 2, 3 and 4 fixed in a vertical attitude by means of a clamp 45.

Figure 10:
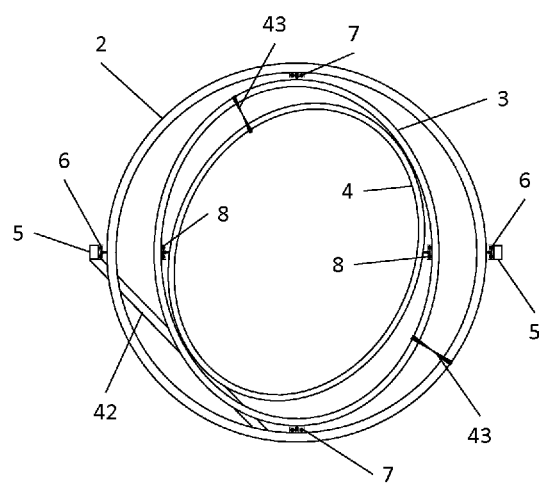
FIG. 10 shows a plan view of the arrangement of FIG. 8 with the platform omitted where the middle and inner ring are constrained to rotate with the use of elasticated bands.

In FIG. 10, it can be seen that rotational movement between the rings of FIG. 8 is constrained through the use of a stretchable elasticated material 43. In this configuration the platform 41 of FIG. 8 will wobble in two dimensions.

Figure 11:
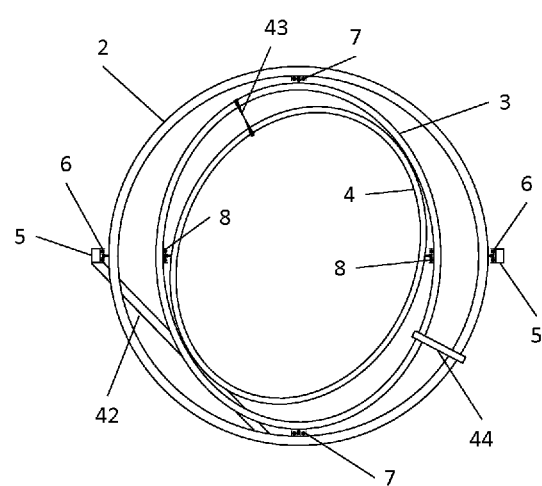
FIG. 11 shows a plan view of the arrangement of FIG. 8 with the platform omitted and where the middle ring is fixed in position and the inner ring is constrained to rotate with the use of an elasticated bands.
Figure 12:
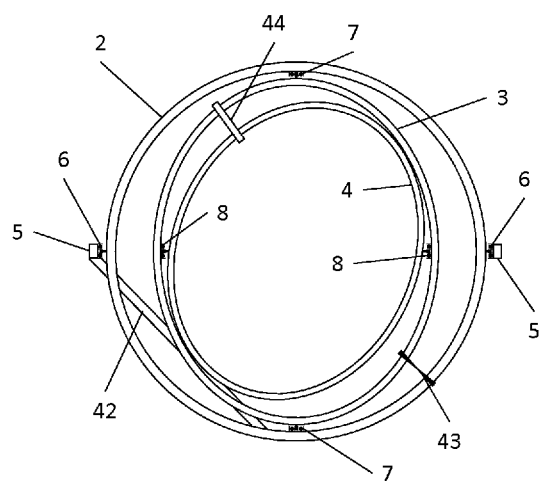
FIG. 12 shows a plan view shows a plan view of the arrangement of FIG. 8 with the platform omitted where the inner ring is fixed in position relative to the middle ring, which is constrained to rotate with the use of a stretchable band.

In FIG. 11, in a further development of the arrangement of FIG. 8 the rotational movement between the middle ring 3 and outer ring 2 is prevented through the use of a clamp 44. Rotational movement between the inner ring 4 and middle ring 3 continues to be constrained through the use of a stretchable band 43. In FIG. 12, by contrast, the positions of the stretchable elasticated material 43 and clamp 44 are interchanged such that the rotational movement between the inner ring 4 and middle 3 is prevented but rotational movement between the middle ring 3 and the outer ring is instead constrained. In the configurations of FIGS. 11 and 12 the platform 41 of FIG. 8 will wobble in one direction, the direction of FIG. 11 being orthogonal to that of FIG. 12

Figure 13:
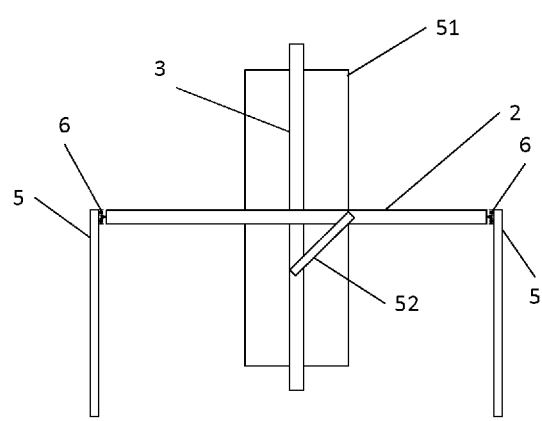
FIG. 13 show a side view of the activity frame of this invention arranged as a jogging wheel.
Figure 14:
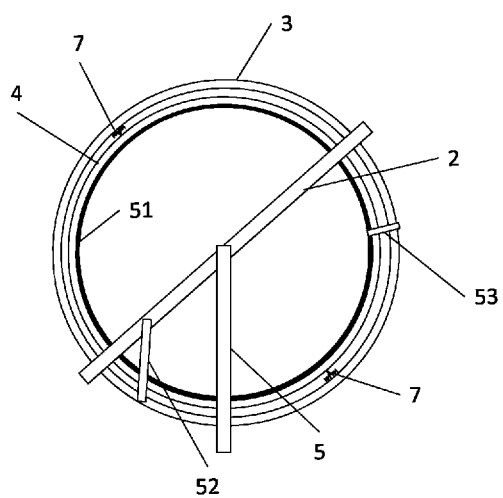
FIG. 14 shows the arrangement of FIG. 13 seen from another side.

FIGS. 13 and 14 show the activity frame of the invention arranged as a jogging wheel. A short open ended cylinder 51 is mounted within the inner ring 4 and coaxially with it. The middle ring 3 is fixed in position, using a clamp 52, with respect to outer ring 2. The inner ring 4 is fixed in a co-planer relationship with middle ring 3 by a further clamp 53. In this configuration the cylinder 51 is free to rotate about an axis through the pair of diametrically opposed bearings 6 supporting outer ring 2. An individual within cylinder 51 running, jogging or walking around the inner perimeter of cylinder 51 will cause it to rotate as described. Thus this configuration will form a tread-mill for play, fitness or training purposes. Omitting clamp 53, will allow the cylinder to swing; omitting clamp 52 will allow the cylinder to tip.

Figure 15:
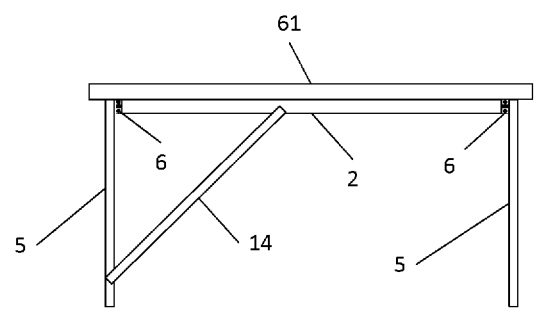
FIG. 15 shows a side view of the activity frame of the invention arranged to provide a flat elevated base.

In FIG. 15 the three concentric rings are supported as in FIG. 1 but with a platform 61 mounted or resting on the three rings. A clamp 14 fixes outer ring 2 to a support 5 (or other fixed object) such that ring 2 and platform 61 is horizontal. The platform 61 constrains middle ring 3 and inner ring 4 into a coplanar relationship with outer ring 2. This arrangement provides a flat elevated play platform. In a variation of this arrangement the platform comprises a wide circular frame on which a plurality of springs is mounted supporting a canvass mat within the circular frame, this arrangement acting as a trampoline.

Figure 16:
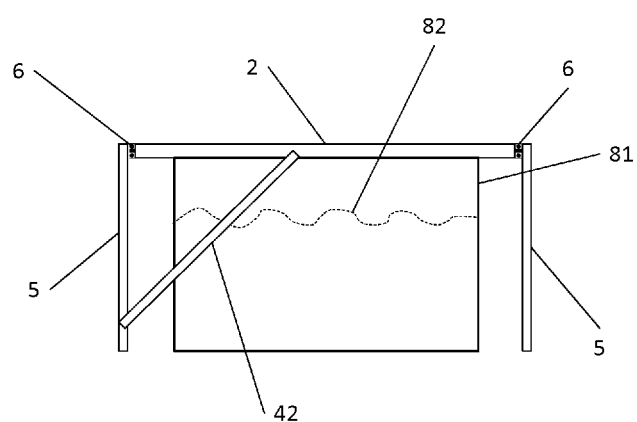
FIG. 16 shows a view of a further arrangement where a water tank is supported by the rings locked in a horizontal position.

In FIG. 16 the three concentric rings are supported as in FIG. 1 but with a rigid or flexible tank 81 attached to the inner ring 4 and containing water 82. The outer ring 2 is attached to the supports 5 by means of a clamp 42. The outer ring 2 and is fixed to the middle ring 3 and the inner ring 2 by means of a suitable clamp (not shown). This arrangement can be used as a small swimming or paddling pool or Jacuzzi.

Figure 17:
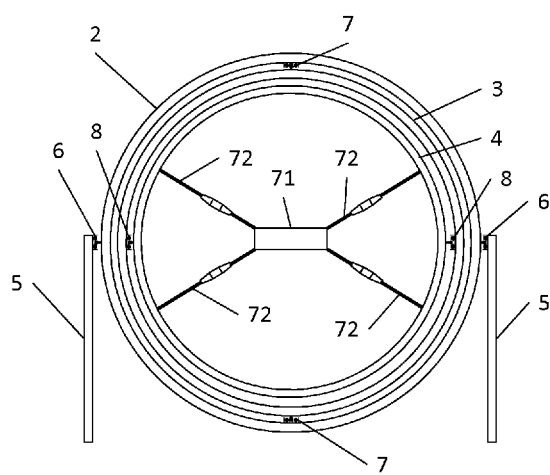
FIG. 17 shows a side view of the activity frame arranged to support a tension ring.
Figure 18:
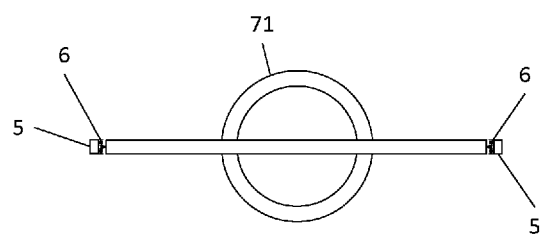
FIG. 18 is a plan of the arrangement of FIG. 17.

In FIGS. 17 and 18 a ring 71 is held in position centrally and transversely to inner ring 4 via four adjustable tension cables 72. The ring 2, 3, 4 can either be free to move or be fixed in a vertical coplanar relationship with clamps to act as a tension ring fitness or play device.

The illustrations in FIGS. 2 to 18 are intended to illustrate possible configurations for the set-up of the activity frame of the invention. It will be apparent that many other arrangements are possible. Examples include: Configurations include:
  fixing the rings at angles to one another and to the base to form a climbing frame;
  fitting a slide to the horizontal platform of the sixth configuration;
  fixing the rings at angles to one another with a slide attached to the outer ring;
  suspending one or more swings from one or more of the rings;
  placing a playhouse, fort, castle or the like on the horizontal platform of the sixth configuration;
  hanging a sun-lounger from one of the rings normally the outer ring fixed in position by a clamp to one of the opposed supports or to a fixed object. The other rings are clamped to one another at an angle to the outer ring and may have a shade can be attached to one of them;
  fixing the rings at angles to one another with ropes or netting joining the rings together to form a scrambling frame;

By adding a variety of other accessories the activity frame can be used for a huge variety of purposes.

Activity frames, and in particular their rings can be made in a variety of ways, including using additive manufacturing methods (3D printing).

The invention claimed is:

1. An activity frame comprising a first or outer ring mounted between a pair of opposed bearings in an opposed pair of supports, the first bearings having a first common axis; a second or middle ring mounted between opposed bearings on the first ring, the bearings on the first ring having a second common axis orthogonal to the first common axis; a third or inner ring mounted between opposed bearings on the second ring, the bearings on the second ring having a third common axis orthogonal to the second axis; and in which the activity frame comprises demountable restraining means configured, when the activity frame is in use, to fix two or more of the rings in multiple positions with respect to one another, and demountable bars configured to fix one or more of the rings to the frame or other fixed object, when the activity frame is in use, in a range of different ring positions relative to the supports.

2. An activity frame according to claim 1 in which the demountable restraining means comprises one or more clamps detachable from the activity frame.

3. An activity frame according to claim 1 in which the demountable restraining means comprises at least two actuators or motors attached one each to different rings.

4. An activity frame according to claim 1 further comprising a sphere mounted within the inner ring, the sphere comprising a closable opening.

5. An activity frame according to claim 4 in which the sphere comprises deformable material supported in a spherical shape by a mesh.

6. An activity frame according to claim 1 further comprising a cylindrical tub or barrel mounted within the inner ring.

7. An activity frame according to claim 6 in which the restraining means comprises a bar attached both to the inner ring and the middle ring and in which the inner ring and the middle ring are co-planer.

8. An activity frame according to claim 1 further comprising a wobble platform attached to the inner ring.

9. An activity frame according to claim 1 further comprising an open ended cylinder mounted within the inner ring, the open ended cylinder being co-axial with the inner ring.

10. An activity frame according to claim 1 further comprising one or more or clamps holding the inner, middle and outer rings in a co-planer horizontal relationship, and in which the outer ring is fixed in a horizontal plane by a further clamp to at least one of the supports or to a another fixed object, and further comprising a water vessel mounted within the inner ring, the water vessel being co-axial with the inner ring.

11. An activity frame according to claim 1 further comprising a tension ring mounted within the inner ring, a plane of tension ring being substantially transverse to the plane of the inner ring.

* * * * *